United States Patent [19]

Gyarmati et al.

[11] 4,199,560
[45] Apr. 22, 1980

[54] SOLID ORAL PHARMACEUTICAL PRODUCT WITH INCREASED EFFICACY AND PREDETERMINED STEADY STATE OF SOLUBILITY

[75] Inventors: László Gyarmati; István Rácz; Peter Szentmiklósi; János Plachy, all of Budapest, Hungary

[73] Assignee: Novex Talalmanyfejleszto Es Ertekesito Kulkereskedelmi Rt, Budapest, Hungary

[21] Appl. No.: 952,932

[22] Filed: Oct. 19, 1978

[30] Foreign Application Priority Data

Feb. 24, 1978 [HU] Hungary .................................. 1247

[51] Int. Cl.² .......................... A61K 9/22; A61K 9/26; A61K 9/54; A61K 33/06
[52] U.S. Cl. ........................................ 424/19; 424/22; 424/154; 424/155; 424/157; 424/158
[58] Field of Search ..................... 424/19-22, 424/34, 38, 154, 158, 361, 363

[56] References Cited

U.S. PATENT DOCUMENTS

| | | | |
|---|---|---|---|
| 2,146,867 | 2/1939 | Welin | 424/34 |
| 2,166,868 | 7/1939 | Jones | 424/34 |
| 2,774,710 | 12/1956 | Thompson et al. | 424/155 |
| 2,793,979 | 5/1957 | Svedres | 424/22 |
| 2,805,977 | 9/1957 | Robinson et al. | 424/38 |
| 2,836,540 | 5/1958 | Hardt | 424/155 |
| 2,854,376 | 9/1958 | Hardt | 424/363 |
| 2,875,130 | 2/1959 | Grass et al. | 424/38 |
| 3,062,720 | 11/1962 | Costello | 424/22 |
| 3,079,303 | 2/1963 | Raff et al. | 424/34 |
| 3,108,046 | 10/1963 | Harbit | 424/38 |
| 3,175,942 | 3/1965 | Anderson et al. | 424/158 |
| 3,362,880 | 1/1968 | Jeffries | 424/22 |
| 3,555,151 | 1/1971 | Kaplan et al. | 424/156 |
| 3,579,634 | 5/1971 | Brown | 424/154 |
| 3,944,660 | 3/1976 | Gottfried et al. | 424/158 |

Primary Examiner—Shep K. Rose
Attorney, Agent, or Firm—Young & Thompson

[57] ABSTRACT

The present invention relates to a solid oral pharmaceutical preparation with protracted release of the active ingredient consisting of discrete solid granules containing the active ingredient soluble in the stomach and auxiliary agents and of an equally solid external phase surrounding the said granules, whereby the granules forming the internal phase consist of granules prepared from a powder mixture which contains as active ingredient, or in addition to it a non-toxic metal compound, being capable of binding an acid, and being insoluble or but slightly soluble in neutral aqueous medium—particularly bismuth, aluminium or magnesium compound—and auxiliary materials prepared with an aqueous emulsion containing a hydrophobic component and hydrophylic emulsifiers, and the external phase contains a solid, dry, amphoteric gel forming substance in an amount of 1-50 percent w/w related to the total weight of the preparation in admixture with auxiliary agents.

The preparation is produced by the wetting of the powder mixture containing the basic metal compound, auxiliary material and in given case additional active ingredient with the aqueous emulsion of the hydrophobic component prepared by applying the hydrophylic emulsifiers then by granulation and admixing the dried granules with the amphoteric gel forming substance, and pressing it into tablets, or filling into capsules.

3 Claims, No Drawings

SOLID ORAL PHARMACEUTICAL PRODUCT WITH INCREASED EFFICACY AND PREDETERMINED STEADY STATE OF SOLUBILITY

The present invention is directed to a solid oral pharmaceutical preparation with protracted action consisting of discrete solid granules containing the active ingredient and an equally solid external phase surrounding the said granules whereby the granules forming the internal phase consist of granules prepared from a powder mixture which contains as active ingredient, or in addition to it a metal compound, being capable of binding an acid, and being insoluble or but slightly soluble in water—particularly bismuth, aluminium, or magnesium compound—and usual pharmaceutical auxiliary materials prepared with an aqueous emulsion containing a hydrophobic organic substance, particularly stearic, or palmitic acid, and a hydrophylic emulsifier; and the external phase containing an amphoteric gel forming substance, particularly tragacanth in admixture with usual pharmaceutical auxiliary agents, particularly carriers and/or lubricating agents.

The invention gives a solution of a very important problem in the field of antacid therapy. Though it is well known that hyperacidity does not cause such ulcers, it can be a condition of their formation; ulcer forms only on surfaces exposed to the effect of hydrochloric acid. The presence of excess hydrochloric acid prevents the curing of ulcer already formed, so the therapy requires a proper diet and in given case, besides observing other instructions, the neutralization of the excess acid to a proper degree. Thus the acid binding medicine for the given purpose must satisfy the following requirements:

the initial neutralizing effect must be quick and must keep its efficacy during the normal digestion time of the stomach;

it must bind the required amount of acid;

it must raise the pH value of the gastric acid to a level at which the pepsin activity is of reduced value but not fully inhibited;

it may not cause a higher rise in the pH value of the gastric acid than desired;

it should not cause a systemic alkalosis even when applied repeatedly and for a long time.

The findings of a great number of tests conducted at a clinic in cases of hyperacidity show that the best acid binding effect can be expected from preparations whose on-time dose at a pH of 3 in a simulated gastric acid of 3 pH /measured by constant pH method/ keep their acid binding effect through the retarded release of the active ingredient for at least an hour and during this time it continuously reacts with 7–10 ml of hydrochloric acid while maintaining constant pH of 3.

According to the state of art pharmaceutical preparations on the market applied in case of hyperacidity show a divergent picture as to their acid binding ability. /Steiberg et al: J. Pharm. Sci. 54, 625. § 1965. Matts S.G., et al., Brit. Med. J. 1.5437: 753–756/1965/. E.g. the research of Mr. Beckmann is already directed to the introduction of a preparation which has an effect prolonged in time. However, the dried aluminium-hydroxide-magnesiumcarbonate gel was not able even in vitro conditions to keep the chemical reaction of the gastric acid at the required level during the total period of normal biological digestion.

In conformity with the findings of the above authors and similarly to our results most of the antacid preparations lose their acid binding ability in 8–10 minutes, i.e., they are not capable of further neutralizing the hydrochloric acid forming continuously during the normal digestion time.

This efficiency can be diminished only partly in the case of antacid preparations by changing the composition of the acid binding ingredients. It is well known that in preparations containing carbonates, these carbonates mostly react in a moment with gastric acid thus they not only fail to exert a retarded effect but also release $CO_2$ which irritates the wall of the stomach and consequently stimulates the cells of mucous membranes to produce even more hydrochloric acid.

By the application of acid binding agents exerting their effect more slowly and without releasing $CO_2$ such as magnesiumoxides or aluminiumhydroxide, these disadvantages can be overcome to a great extent, but none of the preparations containing the most favourable combination of acid binding agents prepared by the known method can bring about an effect lasting for more than 8–10 minutes mentioned above, consequently none of the agents prepared by the known methods is capable of at least partly satisfying the requirements summed up in the foregoing.

Our invention relates to controlled release two-phase solid oral pharmaceutical compositions /tablets, coated pills, capsules/ with protracted action and comprises the granulation of a powder mixture which contains the active ingredient, a solid carrier, and optionally pharmaceutical auxiliary agents with a liquid consisting of an aqueous emulsion which contains hydrophobic and hydrophylic components, said granules being surrounded by an equally solid external phase which owing to its specific physico-chemical properties further increases the release time of the active ingredient to a significant extent thereby augmenting the protracted biological utilization of the active ingredient to a level approaching the theoretical optimum and pressing the granules thus obtained into tablets or filling the same into capsules. The special granulating emulsion contains as hydrophobic component stearic, or palmitic acid, while as hydrophylic components two types of non-ionic surface active agents, namely Tween-type emulsifiers, and optionally a mucus forming substance e.g. sodium carboximethyl-cellulose. By appropriate selection of the components of the emulsion and changing their quantitative ratio the rate of release of the active ingredient could be modified.

The present invention is based on the recognition that acid binding metal compounds being generally insoluble in water in neutral medium—like basic bismuth nitrate, aluminium hydroxide, magnesium hydroxide, magnesium trisilicate and other substance of amphoteric character used as active ingredient in antacidic preparations—enter into molecular interaction at an approximately neutral pH inverval with gel-forming substances of vegetal or animal origin e.g. tragacanth, albumin, casein, pectin, etc. and form a sticky homogeneous mass of gel-like structure and strongly increased viscosity from which the basic metal compound is released extremely slowly and uniformly even in acidic medium. Thus in the case of the antacid preparation containing the basic metal compound itself as active ingredient the acid binding capacity of the composition in the stomach is maintained at a uniform level for a long period of time, while if a composition is used which contains in addition to the slow releasing basic metal compound also other active ingredients, the latter is also released from the mass formed in the stomach from the composition at a similarly slow, uniform rate.

This surprising phenomenon can be illustrated experimentally in the following simple manner:

In 1 percent aqueous tragacanth mucus 10, 15, or 20 percent w/w of finely powdered basic bismuth nitrate is suspended. The homogeneous suspensions are divided into equal portions and the pH value of the samples is adjusted to 2, 3, 4, 5, 6, 7, 8 and 9, respectively by adding a few drops of diluted hydrochloric acid or diluted aqueous sodium hydroxide solution /the own pH value of the suspension is to about 4.5/. Thereafter the viscosity of the samples kept at a temperature of 23° C. is measured by a Hoppler-type rehoviscosimeter at certain intervals. Since tragacanth binds alkali to a certain extent, the pH value of the samples is checked and if necessary corrected several times in the course of the experiment.

In Table I are compared the viscosity values of the sample series containing basic bismuth nitrate in varying concentrations at various pH values with those of tragacanth mucus having the same concentration /1%/ and pH value but not containing basic bismuth nitrate. The said viscosity values were measured 40 minutes, 3 hours and 16 hours respectively after the preparation of the suspension. The $\eta_e$ equilibrium viscosity values measured at 23° C. are shown as a function of the pH.

The obtained viscosity values clearly show that between pH 4 and 7 the samples containing the metal compound behave in quite a different manner than in a more strongly acidic or alkaline interval. Between the above pH values the viscosity extremely increases and reaches several fold the initial value, then the maximal value remains practically the same for a longer period of time. The macroscopic picture of suspensions having different pH values reveal a similarly conspicuous difference; the following table shows the changes observed during 48 hours in a 10 percent suspension.

solid antacid preparations of such composition in the beginning the tragacanth is in excess related to the basic bismuth nitrate, at first it is the basic bismuth nitrate which is in significant excess, because the solvation of tragacanth is protracted, taking place only gradually. In this case, however, the reaction proceeds rapidly and the equilibrium viscosity can increase to manifold of the initial value within 30 minutes.

The velocity of gelation strongly depends on the concentration of the basic bismuth nitrate and other basic metal compounds suspended in the tragacanth mucus as well.

The high increase of the viscosity of the suspensions with nearly neutral weakly acidic pH, and the further fact that while in acidic or alkaline suspensions the suspended metal compound does not undergo physical changes and with time precipitates from the tragacanth mucus, in nearly neutral suspensions the originally suspended metal compound itself jelifies, and after a certain time the whole suspension becomes a homogenous jelly-like gel, both clearly show that the suspended originally insoluble basic metal compounds enter into molecular reaction with the amphoteric gel forming substance, the tragacanth, and a homogeneous, sticky jellylike mass is formed which contains the metal compound bound in gel form.

The above experiments were repeated in a similar manner except that basic bismuth nitrate was replaced by another acid binding metal compound which is insoluble or but slightly soluble in water /e.g. aluminum hydroxide or magnesium hydroxide/; similar results were achieved. In our experience as amphoteric gel forming substances, pectin or albumin can also be used. These experimental results show that the above discussed behaviour can be regarded as a general property of acid binding inorganic metal compounds insoluble in water in neutral medium and of amphoteric gel forming substances.

It has been found that this property of the above mentioned compounds can be advantageously made use Table The macroscopically observable behaviour of a suspension containing 10 percent basis bismuth nitrate in 1 percent tragacanth mucilage at different pH values of the medium

| pH | Directly after preparation | 8 hours | 16 hours | 24 hours | 48 hours |
|---|---|---|---|---|---|
| 2-3 | homogenous susension | slightly sedimented suspension | progressed sedimentation | completely sedimented suspensions; the sedimented part is not gelatinous, it is powder-like; the supernatant liquid is of mucilaginous consistency | |
| 4 | homogenous suspension | thick-flowing, homogenous suspension | gelatinous, thick, mucilaginous suspension | homogenous gels of gelatinous consistency | gelatinous gels with starting syneresis, the separated liquid is not of mucilaginous consistency |
| 5-6 | homogenous suspension | thick-flowing, homogenous suspension | homogenous, gelatinuous gel | | |
| 7 | homogenous suspension | thick-flowing, homogenous suspension | gelatinizing, thick mucilaginous suspension | | |
| 8 | homogeous suspension | slightly sedimented suspension | progressed sedimentation | Completely sedimented suspensions; the sedimented part is slightly gelatinous, the supernatant liquid is of mucilaginous consistency | |
| 9 | homogenous suspension | slightly sedimented suspension | progressed sedimentation | Completely sedimented suspension; the sedimented part is of powdery character, the supernatant liquid is of mucilaginous consistency | |

For the interpretation of the reaction between basic bismuth nitrate and tragacanth it must be taken into consideration that the reaction occurs only with solvated tragacanth. From this it follows that although in of in pharmacy, first of all for the production of antacid pharmaceutical preparations which exert their action in the stomach uniformly for a longer period due to the controlled, strongly protracted, uniform release of the acid binding active ingredient. If the said metal compounds are surrounded with such amphoteric gel forming substance when coming into contact with gastric acid in the stomach, then the described gel forming process starts in the stomach itself under the effect of the nearly neutral or weakly acidic pH value formed "in situ" as a result of the beginning diffusion of the metal compound. The formed strongly viscous, sticky jelly-like mass including the acid binding metal compound, adheres to the stomach wall and exerts its action uniformly for a longer period of time, in an optimal manner, corresponding to the physiological requirements. This optimal mode of action, complying with theoretical considerations was substantiated by clinical tests carried out with telemetric Heidelberg capsule, and coloured pictures taken in situ in the stomach with glass filter optics.

Although the primary field of application of the present invention is the production of antacid preparations—namely in this case the antacid active ingredient itself serves as basic metal compound required to obtain the desired effect,—the present invention may be advantageously used for the production of any pharmaceutical preparation from which the active ingredient is uniformly and protractedly released within the desired long period of time /e.g. compositions having spasmolytic, hypnotic or antihistaminic effect/ if this active ingredient is combined with an acid binding metal compound expediently e.g. aluminum hydroxide, providing for the protracted release of this active ingredient in the above described manner.

In solid pharmaceutical compositions for oral use the optimal level of protracted release of the active ingredient following the interaction of the acid binding metal compound and the amphoteric gel forming substance in the stomach can be ensured by preparing granules from the powder mixture of the acid binding metal compound and the powdered form of pharmaceceutical carrier substances, and optionally a pharmaceutical auxiliary agent and/or a further active ingredient with an aqueous emulsion containing a hydrophobic component, preferably stearic acid, or palmitic acid, and hydrophylic emulsifier; the granules thus obtained are mixed prior to tabletting or filling into capsules with a dry powder mixture, which—in addition to the carriers or other auxiliary substances, e.g. lubricant—contains a gel forming substance of amphoteric character, preferably tragacanth in a sufficient quantity to ensure the mucus concentration required for the above described gel formation when reaching the stomach. This means that to the dried granules, beside the usual lubricants and/or other auxiliary materials an amphoteric gel forming substance most expediently tragacanth is admixed in a quantity corresponding to 80–800 percent w/w of the included metal compound, and this inhomogeneous mixture consisting of solid granules and the powder mixture constituting the external phase is compressed to tablets or filled into capsules by the method used in pharmaceutical practice.

According to an advantageous method of preparation of the granules forming the internal phase the granulation of the powder mixture containing the active ingredient, the carrier and optionally other auxiliary agent is carried out by using an aqueous emulsion which contains as hydrophobic component stearic acid or palmitic acid mentioned above and as hydrophylic component two different non-ionic emulsifiers, whereby the two different surface active agents and their quantitative ratio are preferably selected so that the so called HLB /hydropholic-lipophile balance/ of the emulsifying system—being characteristic of the emulsifying capacity—should be between 8 and 12, preferably about 10.

Namely each emulsifying system can be characterized by the necessary HLB value /see Griffin W. C., J. Soc. Cosmetic. Chem. 5, 249 /1954/; Racz I., Acta Pharm. Hung. 34, 26. /1964//, ensuring optimal stability in a given system from the aspect of emulsifying.

The necessary HLB values of a given emulsifying system /$HLB_{sz}$/ are as follows:

$$HLB_{sz} = \frac{W_A \cdot HLB_A + W_B \cdot HLB_B B + W_C \cdot HLB_C}{W_A + W_B + W_C}$$

wherein $W_A$ and $W_B$ are the weights of both emulsifiers /A and B/ in g in an emulsion resulting in ideal physical stability, $W_C$ etc. are the weight of the optional further emulsifier in g /C etc. such as sodium carboxymethyl cellulose/ $HLB_A$, $HLB_B$ etc. are the own HLB values of the substances in caption from literature or can be measured by the method of I. Racz and E. Orban /J. Coll. Sci. 20, 99./1965//.

Theoretical calculation based on the HLB value of the components of the granulating emulsion enables the selection of the composition ratio which is optimal from the point of view of the retardation of the active ingredient release whichever emulsifier is used. On the basis of calculations of the HLB values of non-ionic emulsifiers to be considered primarily applicable /polyoxyethylene-sorbitan-monooleates, polyoxyethylene-sorbitan-monolaurates, polyoxyethylene-sorbitan-monostearates and monopalmitates, sorbitan fatty acid esters/ it may be stated as a practical rule that generally satisfactory results may be obtained if the amount of the hydrophobic component /e.g. stearic acid/ emulsified in the granulating liquid is taken as 25 parts by weight, the two different non-ionic emulsifiers are used in a ratio 1–7, preferably 1–3 parts by weight. It is particularly preferable to add beside the two non-ionic emulsifiers a mucus forming substance, preferable 5–7 parts by weight of sodium carboxymethyl cellulose to the granulating emulsion. Such granulating emulsions are expediently prepared by dissolving the hydrophobic component in double amount of alcohol under warming, adding the emulsifier to the solution thus obtained, and emulsifying the still warm alcoholic solution in an approximately five fold amount of water or advantageously in a sodium carboxy-methyl-cellulose solution having a concentration of about 2 percent.

The granulating emulsion thus obtained is then used for the granulations of the powder mixture containing active ingredient, carrier and optionally other auxiliary agents. Two parts by weight of the powder mixture are admixed and kneaded preferably with 1 part by weight of granulating emulsion and the wet mass granulated by known methods e.g. by pressing through a sieve. To the dried granules the amphoteric gel forming substance is added in an amount of 1–50 percent w/w—related to the total weight of the finished preparation—optionally in the presence of an auxiliary agent such as a carrier and/or lubricating agent, expediently magnesium stearate, whereafter the mixture obtained is pressed into tablets or filled into capsules.

According to a further preferred embodiment of the present invention in addition to or instead of the already mentioned mucus forming substance an amphoteric gel forming agent /e.g. tragacanth/ may also be added to the powder mixture, preferably in the same amount as the basic metal compound present in the powder mixture. Thus, a composition is prepared in which the amphoteric gel forming substance is present not only in the external phase surrounding the granules, but also inside the granules which form the internal phase; this further promotes the rapid interaction between the basic metal compound and the amphoteric gel forming substance discussed above.

Thus, the present invention relates to a solid oral pharmaceutical preparation with protracted action—mainly tablets or capsules—consisting of discrete solid granules which contain the active ingredient soluble in the stomach and auxiliary agents, and of an equally solid external phase surrounding the said granules whereby the granules forming the internal phase consist of granules prepared from a powder mixture which contains as active ingredient or in addition to it a metal compound being capable of binding an acid and insoluble, or but slightly soluble in water, in neutral medium—particularly a bismuth, aluminum, or magnesium compound—and auxiliary agents with an aqueous emulsion containing a hydrophobic component and hydrophyl emulsifiers; and the external phase contains a solid amphoteric gel forming substance in an amount of 1–50 percent w/w related to the total weight of the composition, and auxiliary agents.

The active ingredient content of the granules forming the internal phase is preferably 30–80 percent w/w. In the case of antacid compositions the said active ingredient is the acid binding metal compound itself, preferably basic bismuth carbonate, basic bismuth nitrate, aluminium hydroxide, or magnesium trisilicate, while if the composition contains active ingredients having other effects, /e.g. spasmolytics/, the granules contain beside 1–60 percent w/w of such an active ingredient, preferably 40–80 percent w/w of acid binding metal compound which is insoluble, or but slightly soluble in water in neutral medium, expediently aluminium hydroxide.

The granules forming the internal phase contain as hydrophobic component derived from the granulating emulsion, preferably 2–10 percent w/w of stearic acid of palmitic acid; as hydrophylic component preferably two different non-ionic emulsifyiers, particularly polyoxethylene-sorbitan monooleate, polyoxethylene-sorbitan-monolaurate, -monostearate, and/or monopalmitate, or sorbitan-fatty acid esters in a total amount of 0.5–5 percent w/w of a mucus forming substance, preferably sodium carboxymethylcellulose, sodium alginate, and/or an amphoteric gel forming substance, particularly tragacanth.

Further details of the present invention are to be found in the examples without limiting the scope of the claims to the examples.

EXAMPLE 1

For the production of a tabletted preparation the following quantities of substances are used per tablet:

| | |
|---|---|
| Magnesium trisilicate | 0.28 g |
| Magnesium oxide | 0.12 g |
| Bismuth subnitrate | 0.05 g |
| Tragacanth | 0.05 g |
| Sodium carboxymethylcellulose | 0.035 g |

The above listed substances, complying in quality with the requirements of the Pharmacopoeia and milled to comply in powder fineness with the requirement for "fine powder" /sieve No.V/ of the Pharmacopoeia, are mixed to form a homogenous mixture, then kneaded with a granulating liquid prepared as follows:

Three hundred /300/ g of stearic acid is dissolved in 300 g of 96 percent alcohol under heating; then 70 g of "Tween 85" and 20 g of "Tween 20" emulsifiers /non-ionic emulsifier of polyoxyethylene-sorbitan-monooleate base/ are admixed and the alcoholic mixture is emulsified still warm in 3500 g of an aqueous, 4 percent carboxymethylcellulose sodium mucilage. This emulsion is used, for the preparation of the tablets, according to the usual method; the powder mixture of the above specified composition is mixed in 2:1 weight proportion with the granulating emulsion and kneaded, then the obtained wet mass is passed through a sieve, dried, the usual finishing and lubricating substances /e.g. magnesium stearate, Aerosil R 972/, as well as 0.02 g tragacanth per tablet are admixed and the mixture is pressed into tablets of 0.76 g each.

The tablets thus prepared remain in the stomach adhering to the gastric wall for longer periods than the usual preparations. In simulated gastric fluid in which the pH is maintained constantly at 3, measured by the so-called "constant pH=3 method", each tablet consumed 5.3 to 6.2 milliequivalent of hydrochlor acid per hour, at a constant rate.

EXAMPLE 2

Proceeding also as described in Example 1, for completing the tablet mass, the following materials are used for 1 tablet-also in quality complying with the requirements of the Pharmacopoeia:

| | |
|---|---|
| Magnesium trisilicate | 0.25 g |
| Sodium alginate | 0.12 g |
| Magnesium oxide | 0.10 g |
| Calcium lactate | 0.06 g |
| Tragacanth | 0.06 g |
| Bismuth subnitrate | 0.05 g |
| Sodium carboxymethylcellulose | 0.04 g |

The granulating liquid is applied in a composition and quantitative ratio as given in Example 1, and proceeding as described above a tabletted preparation is produced the properties of which are essentially identical with those indicated in Example 1. Similarly good results may be obtained by the application of any emulsifying system of different HLB value.

In the following we present some advantageously applicable emulsifying combinations and the calculation of the HLB values of the emulsifying systems consisting of the components cited above:

| 1. Components | Quantity | HLB-value |
|---|---|---|
| Stearic acid | 50 g | 1 |
| CMC-Na | 60 g | 15 |
| Tween 85 | 60 g | 11 |
| Tween 20 | 20 g | 16.7 |

Resulting HLB-value:

$$\frac{50 \cdot 1 + 60 \cdot 15 + 60 \cdot 11 + 20 \cdot 16.7}{50 + 60 + 60 + 20} = 10.2$$

2.
| Components | Quantity | HLB-value |
|---|---|---|
| Stearic acid | 50 g | 1 |
| CMC-Na | 60 g | 15 |
| Tween-80 | 60 g | 15 |
| Glycerol monostearate | 20 g | 3.8 |

Resulting HLB-value:

$$\frac{50 \cdot 1 + 60 \cdot 15 + 60 \cdot 15 + 20 \cdot 3.8}{50 + 60 + 60 + 20} = 10.1$$

3.
| Components | Quantity | HLB-value |
|---|---|---|
| Stearic acid | 50 g | 1 |
| CMC-Na | 60 g | 15 |
| Span 60 | 20 g | 4.7 |
| Polyoxy-ethylene-stearate | 60 g | 16.9 |

Resulting HLB-value:

$$\frac{50 \cdot 1 + 60 \cdot 15 + 20 \cdot 4.7 + 60 \cdot 16.9}{50 + 60 + 20 + 60} = 10.8$$

The powder mixture granulated with the chosen granulating fluid is mixed with the usual lubricating and finishing additives and after addition of 0.02 g of tragacanth, the granules are tabletted. The constant rate of acid neutralization reaction of the tablets thus prepared will vary in accordance with the HLB value of the granulating liquid.

EXAMPLE 3

Production of a preparation filled into gelatin capsules. The process is as described in the previous examples, but the powder mixture containing the active ingredient is prepared from the ingredients listed below, corresponding in quality to the requirements of the Pharmacopoeia, calculated for 1 capsule: ca

| | |
|---|---|
| Magnesium trisilicate | 0.20 g |
| Magnesium oxide | 0.085 g |
| Bismuth subnitrate | 0.035 g |
| Sodium carboxymethylcellulose | 0.023 g |

The powder mixture is granulated subsequently according to the usual method with the granulating liquid specified in Example 1, then the usual lubricating and finishing materials, and for each capsule 0.07 g of tragacanth is admixed and filled into gelatin capsules of proper size in quantities corresponding to 1 dose for each capsule. After ingestion the content of the medicated capsules thus prepared, entering the stomach adhers to the gastric wall and remains in the stomach for a more prolonged time than usual and in the meantime the slowly released active ingredient gradually reacts with the hydrochloric acid present in the stomach. Measured by the previously mentioned "constant pH=3" method, each capsule consumes 4.4 to 5.2 milliequivalent of hydrochloric acid per hour at a uniform rate.

EXAMPLE 4

For the production of a preparation filled into gelatin capsules we proceed as described above, but the powder mixture containing the active ingredient is prepared from the following materials, corresponding in quality to the requirements of the Pharmacopoeia, calculated for 1 capsule:

| | |
|---|---|
| Magnesium trisilicate | 0.20 g |
| Sodium alginate | 0.10 g |
| Magnesium oxide | 0.075 g |
| Calcium lactate | 0.04 g |
| Basic bismuth nitrate | 0.035 g |
| Sodium carboxymethyl-cellulose | 0.023 g |

Subsequently the powder mixture is granulated with any of the indicated granulating fluids according to the usual method, then the usual lubricating and finishing substances are admixed in quantities corresponding to 1 dose for each capsule and after the addition of 0.02 g of tragacanth per capsule, the mixture is filled into capsules of adequate size. The properties of the so obtained medicated capsules are identical to those specified in the previous Example.

EXAMPLE 5

For the production of a preparation filled into gelatin capsules we proceed as described above, but the powder mixture containing the active ingredients is prepared from the following materials, corresponding in quality to the requirements of the Pharmacopoeia, calculated for 1 capsule:

| | |
|---|---|
| Magnesium trisilicate | 0.20 g |
| Magnesium oxide | 0.07 g |
| Aluminium hydroxide | 0.08 g |
| Basic bismuth carbonate | 0.04 g |
| Sodium carboxymethylcellulose | 0.023 g |

Subsequently the powder mixture is granulated with any of the granulating fluids specified in Example 1 according to the usual method, then following addition of the adequate quantities of the usual lubricating and finishing materials 0.06 g of pectin is admixed with the granulated mass and filled into gelatin capsules of adequate size. The properties of the medicated capsules thus obtained are identical to those specified in the previous Example.

EXAMPLE 6

For the production of a preparation filled into gelatin capsules, we proceed as described in the previous Examples, but the powder mixture containing the active ingredients is prepared from the substances listed below, corresponding in quality to the requirements of the Pharmacopoeia, calculated for 1 capsule:

| | |
|---|---|
| Magnesium trisilicate | 0.20 g |
| Magnesium hydroxide | 0.10 g |
| Sodium carboxymethylcellulose | 0.023 g |

Subsequently the powder mixture is granulated with one of the granulating fluids specified in Example 1 according to the usual method, and following addition of the usual lubricating and finishing materials and 0.10 g of gum arabic per capsule, the mixture is filled into gelatin capsules of adequate size. The properties of the medicated capsules thus obtained are identical to those specified in the previous Example.

EXAMPLE 7

The process to be followed is as described in Example 1, but for the preparation of tablets containing a spasmolytic as active ingredient, the following substances are used, calculated for 1 tablet:

| | |
|---|---|
| 3,4,6,7-Tetraethoxy-1-benzal-3,4-dihydro-isoquiline hydrochloride /Drotaverine hydrochloride/ | 0.15 g |
| Tragacanth | 0.20 g |
| Sodium alginate | 0.12 g |
| Aluminium hydroxide | 0.05 g |
| Sodium carboxymethylcellulose | 0.04 g |

The granulating fluid is applied in the same composition and quantitative ratio as described in Example 1 and thus, proceeding further as specified in Example 1, tablets will be produced, the properties of which will be essentially identical to those specified in Example 1.

For the practical illustration of the advantages of the preparations prepared according to the present invention, comparative clinical experiments were performed in human subjects by measuring the duration of action and acid neutralizing effect of the individual preparations.

The experiments were performed in groups of 6 hyperacid volunteers /fasting gastric pH between 0.5 and 2.0/, but free of any other gastro-intestinal disease; simultaneously with antacid capsules prepared according to the method specified in Example 3 /A/ parallel experiments were performed under identical conditions /B/ with tablets without external phase of an amphoteric gel forming substance and /C/ with a known antacid preparation in clinical use containing 400 mg of dried Mg/OH/$_2$+Al/OH/$_3$ gel in the form of tablets of prolonged action, produced by the American Company W. H. Rorer Inc. under the Trade Name Malox® Tablets. Each of the three tablets was administered to the experimental subjects in doses corresponding to 7.00/±0.5/ mEq acid binding agent and the pH value of the gastric juice as well as its changes as a function of time were measured by the aid of Heidelberg capsules /cf.: Conell, A. M., Waters, T. E.: "Assessment of Gastric Function by pH Telemetering Capsule". Lancet 2,227 /1964/; Steinberg, W. H., Mina, F. A., Pick, P. G., Frey, H. G.: "Heidelberg Capsule I. In Vitro Evaluation of a New Instrument for Measuring Intragastric pH." J. Pharm. Sci. 54, 772. /1965//.

In the case of each of the three preparations four parameters were registered after measuring the initial pH values:

1. the time required to reach pH=3,
2. the highest pH value,
3. the duration of the effect at about pH=3,
4. the duration of the effect at about pH=4.

The obtained results /average values obtained for the 6 subjects/ have been summarized in the following table:

| Preparation | /A/ | /B/ | /C/ |
|---|---|---|---|
| Initial pH | 1.2 | 1.1 | 1.0 |
| Time for attaining pH = 3.0 /minutes/ | 8.5 | 6.2 | 5.4 |
| Duration of the effect at pH = 3.0 /minutes/ | 30.0 | 19.0 | 16.6 |
| Duration of the effect above pH = 3.5 /minutes/ | 25.9 | 16.3 | 8.6 |
| Peak pH value | 6.6 | 5.0 | 4.9 |

It can be seen from the tabulated data that the duration of the effect of the two-phase preparation exceeds considerably both the preparation prepared without external phase and the known preparation.

What we claim is:

1. A solid oral pharmaceutical composition with protracted action in the form of tablets or capsules, having an internal phase consisting of solid granules and a solid external phase surrounding the said granules, wherein the granules are prepared from a powdered mixture of the active ingredients and of auxiliary agents granulated with an aqueous emulsion containing 2 to 10% w/w of stearic or palmitic acid, 0.5 to 5% w/w of sodium carboxymethyl cellulose and 1 to 7% w/w of two different non-toxic emulsifiers imparting a HLB-value of 8 to 12, and the said granules contain 10 to 90% w/w of one or more pharmaceutically active compound including at least 5% w/w of a basic bismuth salt insoluble in water in neutral medium, 5 to 20% w/w of a non-toxic gel-forming organic substance selected from the group consisting of sodium carboxymethyl cellulose, sodium alginate and tragacanth and 5 to 7% of solid residue of the said granulating emulsion, and the said solid external phase contains an amphoteric gel-forming substance selected from the group consisting of tragacanth, pectin and sodium carboxymethyl cellulose, in an amount of 1 to 50% of the total weight of the composition, and usual pharmaceutical excipients.

2. A pharmaceutical composition as claimed in claim 1, wherein the granules contain 30 to 80% w/w of at least one basic metal compound capable of binding gastric acid selected from the group consisting of magnesium oxide, magnesium trisilicate, aluminum oxide and aluminum hydroxide, including at least 5% of basic bismuth nitrate or carbonate, 5 to 20% w/w of a non-toxic gel-forming organic substance selected from the group consisting of sodium carboxymethyl cellulose, sodium alginate and tragacanth and 5 to 7% of solid residue of the said granulating emulsion.

3. A process for preparing a solid oral pharmaceutical composition having protracted action, characterized in that a powder mixture containing 30 to 80% w/w of pharmaceutically active ingredients including at least 5% w/w of a basic bismuth salt capable of binding acid and substantially insoluble in water in neutral medium and auxiliary agents including 5 to 20% w/w of a non-toxic organic gel-forming agent is granulated by wetting it with an aqueous emulsion containing 2 to 10% w/w of stearic or palmitic acid, 0.5 to 5% w/w of sodium carboxymethyl cellulose and 1 to 7% w/w of two different non-toxic emulsifiers imparting a HLB-value of 8 to 12, the dried granules are admixed with 1 to 50% by weight, calculated on the total weight of the composition, of a dry powdered amphoteric gel-forming substance selected from the group consisting of tragacanth, pectin and sodium carboxymethyl cellulose and with usual pharmaceutical excipients and the mixture is pressed into tablets or filled into capsules.

* * * * *